United States Patent [19]
Cook et al.

[11] Patent Number: 6,136,794
[45] Date of Patent: *Oct. 24, 2000

[54] PLATELET AGGREGATION INHIBITION USING LOW MOLECULAR WEIGHT HEPARIN IN COMBINATION WITH A GP IIB/IIIA ANTAGONIST

[75] Inventors: Jacquelynn J. Cook, Collegeville; Robert J. Gould, Green Lane; Frederic L. Sax, Villanova, all of Pa.

[73] Assignee: Merck & Co., Inc., Rahway, N.J.

[*] Notice: This patent issued on a continued prosecution application filed under 37 CFR 1.53(d), and is subject to the twenty year patent term provisions of 35 U.S.C. 154(a)(2).

[21] Appl. No.: 09/240,429

[22] Filed: Jan. 29, 1999

Related U.S. Application Data

[60] Provisional application No. 60/073,426, Feb. 2, 1998.

[51] Int. Cl.$^7$ .................................................. A61K 31/725
[52] U.S. Cl. ........................... 514/56; 514/317; 514/331; 514/547
[58] Field of Search .............................. 514/56, 317, 331, 514/547

[56] References Cited

U.S. PATENT DOCUMENTS

| | | | |
|---|---|---|---|
| 4,533,549 | 8/1985 | Lasker | 514/56 |
| 4,603,112 | 7/1986 | Paoletti et al. | 435/235 |
| 4,678,748 | 7/1987 | Sutka et al. | 435/68 |
| 4,739,046 | 4/1988 | Di Luzio | 536/117 |
| 4,761,402 | 8/1988 | Williams et al. | 514/54 |
| 4,877,612 | 10/1989 | Berger et al. | 424/92 |
| 4,877,777 | 10/1989 | DiLuzio | 514/54 |
| 4,971,956 | 11/1990 | Suzuki et al. | 514/55 |
| 4,977,165 | 12/1990 | Oinuma et al. | 514/318 |
| 5,057,503 | 10/1991 | Czop et al. | 514/54 |
| 5,106,616 | 4/1992 | McAnalley et al. | 424/85.2 |
| 5,106,618 | 4/1992 | Beck et al. | 424/85.8 |
| 5,217,883 | 6/1993 | Kaslow et al. | 435/255 |
| 5,288,639 | 2/1994 | Burnie et al. | 435/320.1 |
| 5,374,423 | 12/1994 | Klimpel et al. | 424/85.1 |
| 5,429,818 | 7/1995 | Inzana | 424/256.1 |
| 5,470,835 | 11/1995 | Kirkpatrick et al. | 514/21 |
| 5,531,988 | 7/1996 | Paul | 424/93.4 |
| 5,538,733 | 7/1996 | Emery et al. | 424/422 |
| 5,591,434 | 1/1997 | Jenkins et al. | 424/191.1 |
| 5,763,427 | 6/1998 | Weitz et al. | 514/56 |
| 5,858,378 | 1/1999 | Bostwick | 424/274.1 |
| 5,880,136 | 3/1999 | Duggan et al. | 514/317 |

FOREIGN PATENT DOCUMENTS

| | | |
|---|---|---|
| WO 86/05400 | 9/1986 | WIPO . |
| WO 93/24649 | 12/1993 | WIPO . |
| 97/35579 | 10/1997 | WIPO . |
| 97/35592 | 10/1997 | WIPO . |
| WO 98/23279 | 6/1998 | WIPO . |

OTHER PUBLICATIONS

Cohen et al., "A Comparison of Low–Molecular–Weight Heparin with Unfractionated Heparin for Unstable Coronary Artery Disease", The New England Journal of Medicine, vol. 337, No. 7, pp. 447–452, (Aug. 14, 1997).

Clive Kearon, "Low–Molecular–Weight Heparin versus Unfractionated Heparin for Unstable Coronary Disease", The New England Journal of Medicine, vol. 338, No. 2, pp. 129–130 (Jan. 8, 1998).

Frederick et al., "The Protective Dose of the Potent GPIIb/IIIa Antagonist SC–54701A . . .", Circulation, vol. 93, No. 1, pp. 129–134 (Jan. 1, 1996).

Angus, K., "Cryptosporidiosis and AIDS", *Bailliere's Clinical Gastroenterology*, vol. 4, No. 2, pp 425–441 (Jun. 1990).

Ashman, R. et al., "Production and Function of Cytokines in Natural and Acquired Immunity to *Candida albicans* Infection", *Microbiological Reviews*, vol. 59. No. 4, pp. 646–672 (Dec. 1995).

Derwent Abstract for ZA9209143, Sep. 29, 1993, Acc. No. 93–386927/199348.

Barrios, C. et al., "Mycobacterial heat–shock proteins as carrier molecules. II: The use of the 70–kDa mycobacterial heat–shock protein as carrier for conjugated vaccines can circumvent the need for adjuvants and Bacillus Calmette Guerin priming", *Eur. J. Immunol*, vol. 22, pp. 1365–1372 (1992).

Carrow, E. et al., "Immunoregulation in Experimental Murine Candidiasis: Specific Suppression Induced by *Candida albicans* Cell Wall Glycoprotein", *Infection and Immunity*, vol. 49. No. 1, pp. 172–181 (Jul. 1985).

Cook J. et al., "Visceral Leishmaniasis in Mice: Protective Effect of Glucan", *Journal of the Reticuloendothelial SocietyI*, vol. 27, No. 6, pp. 567–573 (Jun. 1980).

Cook, J. et al., "Immunomodulation of Protozoan Diseases[1,2]", *Surv. Immunol*, Res. 2, pp. 243–245 (1983).

Crawford, F. et al., "Human Cryptosporidiosis", *CRC Critical Reviews in Microbiology*, vol. 16, Issue 2, pp. 113–159 (1988).

Cutler, J. et al., "Enhanced Antibody Responses Induced by *Candida albicans* in Mice", *Infection and Immunity*, vol. 38, No. 3, pp. 1102–1108 (Dec. 1982).

Harp, J. et al., "Protection of Calves with a Vaccine Against Cyrptosporidium Parvum", *J. Parasitol.*, 81(1), pp. 54–57 (1995).

Holbrook, T. et al., "Glucan–Enhanced Immunogenicity of Killed Erythrocytic Stages of *Plasmodium berghei*", *Infection and Immunity*, vol. 32, No. 2, pp. 542–546 (May 1981).

(List continued on next page.)

*Primary Examiner*—Kathleen K. Fonda
*Attorney, Agent, or Firm*—Richard S. Parr; Melvin Winokur

[57] ABSTRACT

A method for inhibiting platelet aggregation in a mammal comprising administering to the mammal a safe and therapeutically effective amount of a GPIIb/IIIa receptor antagonist or a pharmaceutically acceptable salt thereof and a safe and therapeutically effective amount of low molecular weight heparin. A method for inhibiting platelet aggregation in a mammal comprising administering to the mammal a safe and therapeutically effective amount of (2-S-(n-butylsulfonylamino)-3[4-(piperidin-4-yl)butyloxyphenyl]-propionic acid or a pharmaceutically acceptable salt thereof and a safe and therapeutically effective amount of low molecular weight heparin.

5 Claims, No Drawings

OTHER PUBLICATIONS

Holbrook, T. et al., "Immunization of Mice Against Leishmania Donovani by Subcutaneous Injections of Dead Promastigotes", *Am. J. Trop. Med. Hyg.*, vol. 32, No. 1, pp. 51–53 (1983).

Janoff, E. et al., "Cryptosporidium Species, a Protean Protozoan", *Journal of Clinical Microbiology*, vol. 25, No. 6, pp. 967–975 (Jun. 1987).

Jarecki–Black, J. et al., "Resistance Against *Leismania donovani* Induced with an Aluminum Hydroxide Vaccine", *Annals of Clinical and Laboratory Science*, vol. 18, No. 1, pp. 72–77 (Jan.–Feb.) 1988.

Laughon, B. et al., "Prevalence of Enteric Pathogens in Homosexual Men With and Without Acquired Immunodeficiency Syndrome", *Gastroenterology*, vol. 94, No. 4, pp. 984–993 (Apr. 1988).

Maheshwari, R. et al., "Immunoprotection by ⊖–1,3 glucan antigen combination in *Plasmodium berghei* infection in mice", *Indian J. Med Res 89*, pp. 396–403 (Nov. 1989).

Mencacci, A. et al., "A Mannoprotein Constituent of *Candida albicans* That Elicits Different Levels of Delayed–Type Hypersensitivity, Cytokine Production, and Anticandidal Protection in Mice", *Infection and Immunity*, vol. 62, No. 12, pp. 5353–5360 (Dec. 1994).

Nord, J. et al., "Treatment with bovine hyperimmune colostrum of cryptosporidial diarrhea in AIDS patients", *AIDS*, vol. 4, No. 6, pp. 581–584 (1990).

Obaid, K. et al., Protective Effect of L. Donovani Antigens Using Glucan as an Adjuvant, *Int. J. Immunopharmac*, vol. 11, no. 3, pp. 229–235 (1989).

Oblack, D. et al., "Active Immunisation of Mice Against Muscle Damage Mediated by *Candida Albicans*", *J. Med. Microbiol.*, vol. 12, pp. 503–505 (1979).

Peterson, C. et al., CA Abstract No. 120: 189727 WO9324649 A1 (Dec. 9, 1993).

Scaringi, L. et al., "Cell Wall Components of *Candida albicans* as Immunomodulators: Induction of Natural Killer and Macrophage–mediated Peritoneal Cell Cytotoxicity in Mice by Mannoprotein and Glucan Fractions", *Journal of General Microbiology*, vol. 134, pp. 1265–1274 (1988).

Segal, E., "Vaccines Against Fungal Infections", *CRC Critical Reviews in Microbiology*, vol. 14, Issue 3, pp. 229–271 (1987).

Tzipori, S. et al., "Chronic Cryptosporidial Diarrhoea and Hyperimmune Cow Colostrum", *The Lancet*, pp. 344–345 (Aug. 8, 1987).

Ungar, B., et al., "Cessation of Cryptosporidium–Associated Diarrhea in an Acquired Immunodeficiency Syndrome Patient After Treatment With Hyperimmune Bovine Colostrum", *Gastroenterology*, pp. 486–489 (Feb. 1990).

Vazquez, N. et al., "Activation of murine resident peritoneal macrophages by a cell wall extract of *Candida albicans*", *Journal of Medical& Veterinary Mycology*, vol. 33, pp. 385–393 (Jun. 1995).

Williams, D. et al., "Immunization Against Trypanosoma Cruzi: Adjuvant Effect of Glucan", *Int. J. Immunopharmac*, vol. 11, No. 4, pp. 403–410 (1989).

Yamaguchi, H. et al., "immunomodulating Activity of Antifungal Drugs", *Annals of the New York Academy of Sciences*, vol. 685, pp. 447–457 (1993).

PLATELET AGGREGATION INHIBITION USING LOW MOLECULAR WEIGHT HEPARIN IN COMBINATION WITH A GP IIb/IIIa ANTAGONIST

This a continuation of provisional application No. 60/073,426, filed Feb. 2, 1998.

BACKGROUND OF THE INVENTION

Platelet activation and aggregation are involved in unstable angina and acute myocardial infarction, in reocclusion following thrombolytic therapy and angioplasty, in transient ischemic attacks and in a variety of other vaso-occlusive disorders. When a blood vessel is damaged either by acute intervention such as angioplasty, or, more chronically, by the pathophysiological processes of atherosclerosis, platelets are activated to adhere to the disrupted surface and to each other. This activation, adherence and aggregation may lead to occlusive thrombus formation in the lumen of the blood vessel.

The final obligatory step in platelet aggregation is the binding of fibrinogen to an activated membrane-bound glycoprotein complex, GP IIb/IIIa ($\alpha_{IIb}\beta_3$). Platelet activators such as thrombin, collagen, epinephrine or ADP, are generated as an outgrowth of tissue damage. During activation, GP IIb/IIIa undergoes changes in conformation that result in exposure of occult binding sites for fibrinogen. There are six putative recognition sites within fibrinogen for GP IIb/IIIa and thus fibrinogen can potentially act as a hexavalent ligand to crossing GP IIb/IIIa molecules on adjacent platelets. A deficiency in either fibrinogen or GP IIb/IIIa prevents normal platelet aggregation regardless of the agonist used to activate the platelets. Since the binding of fibrinogen to its platelet receptor is an obligatory component of normal aggregation, GP IIb/IIIa is an attractive target for an antithrombotic agent.

Results from clinical trials of GP IIb/IIIa inhibitors support this hypothesis. The monoclonal antibody 7E3, which blocks the GP IIb/IIIa receptor, has been shown to be an effective therapy for the high risk angioplasty population. It is used as an adjunct to percutaneous transluminal coronary angioplasty or atherectomy for the prevention of acute cardiac ischemic complications in patients at high risk for abrupt closure of the treated coronary vessel.

A study reported in *The New England Journal of Medicine* vol. 330, No. 14, pp. 956–961 (1994) showed a decrease from 12.8% to 8.3% in the combined endpoints of death, non-fatal MI and need for urgent revascularization with fibrinogen receptor blockade. This benefit was at the expense of some additional risk of bleeding, with the need for transfusion increasing from 3% to 6%, and the incidence of patients with decreased hematocrit increasing from 7% to 15%. 7E3 was added to the standard regime of heparin and aspirin thus leaving few hemostatic control mechanisms intact. The clinical benefits of this drug could be seen at 6 months.

Many other studies have shown that blocking the GPIIb/IIIa receptor will stop platelet aggregation induced by all of the agonists and thus prevent thrombus formation but leave platelet adhesion relatively intact. The 7E3 monoclonal antibody is described in Coller et al. *Ann. NY Acad. Sci.* 1991; 614: 193–213; and Coller et al. *J. Clin Invest.* 1985; 76: 101–108. Others have used agents based on the RGD sequence, including snake venom proteins, small peptides, and peptidomimetics (Cook et al. *Drugs of Future* 1994; 19: 135–159; and Cox et al. *Medicinal Research Reviews* 1994; 14: 195–228). Integrilin is a cyclic peptide that is based on the KGD sequence in the snake venom protein barbourin (Cook et al. ibid.; and Cox et al. ibid.). It inhibits ligand binding to GPIIb/IIIa but has very little effect on ligand binding to $\alpha_v\beta_3$. Among the non-peptide compounds are RO44-9883 and MK-383, which are administered intravenously, and are also selective for GPIIb/IIIa (Cook et al. ibid.; and Cox et al. ibid.). Orally active agents include SC54684, a prodrug with high oral bioavailability, and RO43-8857, GR144053, and DMP728, which are themselves the active inhibitors (Cook et al. ibid.; and Cox et al. ibid.). Literally thousands of other compounds have been synthesized in an attempt to obtain optimal potency, metabolic stability, receptor specificity, and favorable intravascular survival. Despite variations in these compounds, virtually of all of them retain the basic charge relations of the RGD sequence with a positive charge separated from a negative charge by approximately 10–20 Å (Cook et al. ibid.; and Cox et al. ibid.).

The results of the 7E3 study support the hypothesis that blockade of GPIIb/IIIa receptors is more effective than aspirin in preventing platelet thrombi, even in the presence of heparin. They also support the hypothesis that platelet-dependent thrombi frequently contribute significantly to the development of ischemic complications after PTCA, even when minor mechanical dissections are present.

Heparin is a commonly used anticoagulant. Unfractionated heparin unpredictably binds electrostatically to proteins in addition to tethering to tighten weak antithrombin III:thrombin interactions. Low molecular weight heparin tends to bind in a more predictable pharmacodynamic fashion and is therefore more effective than unfractionated heparin in reducing clot formation. Cohen et al., *N Enyl J Med* 1997; 337:447–52 compares low molecular weight heparin to unfractionated heparin for treatment of unstable coronary artery disease. Patients received 1 mg of enoxaparin (low molecular weight heparin) per kg body weight subcutaneously twice daily, or continuous intravenous unfractionated heparin at a dose adjusted according to the activated partial-thromboplastin time, targeting the activated partial-thromboplastin time at 55 to 85 seconds. All patients received 100 to 325 mg of oral aspirin daily. Results showed that antithrombotic therapy with enoxaparin plus aspirin was more effective than unfractionated heparin plus aspirin in reducing the incidence of ischemic events in patients with unstable angina or non-Q-wave myocardial infarction in the early phase. The benefit with enoxaparin was achieved with an increase in minor but not major bleeding.

SUMMARY OF THE INVENTION

The invention is a method for inhibiting platelet aggregation in a mammal comprising administering to the patient a safe and therapeutically effective amount of a GPIIb/IIIa receptor antagonist or a pharmaceutically acceptable salt thereof and a safe and therapeutically effective amount of low molecular weight heparin. The invention also is the use of a GPIIb/IIIa receptor antagonist or a pharmaceutically acceptable salt thereof, and a safe and therapeutically effective amount of low molecular weight heparin, in the manufacture of a medicament for inhibiting platelet aggregation in a mammal.

The invention is also a method for inhibiting platelet aggregation in a mammal comprising administering to the patient a safe and therapeutically effective amount of a GPIIb/IIIa receptor antagonist or a pharmaceutically acceptable salt thereof, a safe and therapeutically effective amount of low molecular weight heparin, and a safe and therapeutically effective amount of aspirin.

DETAILED DESCRIPTION OF THE INVENTION

One example of the invention is a method for inhibiting platelet aggregation in a mammal comprising administering to the patient a safe and therapeutically effective amount of 2-S-(n-butylsulfonylamino)-3[4-(piperidin-4-yl) butyloxyphenyl]propionic acid or a pharmaceutically acceptable salt thereof (e.g. 2-S-(n-butylsulfonylamino)-3 [4-(piperidin-4-yl)butyloxyphenyl]propionic acid hydrochloride, also called "tirofiban") and a safe and therapeutically effective amount of low molecular weight heparin. A further example of the invention is the use of 2-S-(n-butylsulfonylamino)-3[4-(piperidin-4-yl) butyloxyphenyl]propionic acid or a pharmaceutically acceptable salt thereof, and a safe and therapeutically effective amount of low molecular weight heparin, in the manufacture of a medicament for inhibiting platelet aggregation in a mammal.

Another example of the invention is a method for inhibiting platelet aggregation in a mammal comprising administering to the patient a safe and therapeutically effective amount of 2-S-(n-butylsulfonylamino)-3[4-(piperidin-4-yl) butyloxyphenyl]propionic acid or a pharmaceutically acceptable salt thereof (e.g. 2-S-(n-butylsulfonylamino)-3 [4-(piperidin-4-yl)butyloxyphenyl]propionic acid hydrochloride), a safe and therapeutically effective amount of low molecular weight heparin, and a safe and therapeutically effective amount of aspirin.

The invention takes advantage of the reduced prolongation of bleeding time experienced with, a GP IIb/IIIa receptor antagonist, e.g., 2-S-(n-butylsulfonylamino)-3[4-(piperidin-4-yl)butyloxyphenyl]propionic acid or a pharmaceutically acceptable salt, in combination with low molecular weight heparin, as compared to the extended prolongation of bleeding time associated with the combination of a GP IIb/IIIa receptor antagonist, e.g., 2-S-(n-butylsulfonylamino)-3[4-(piperidin-4-yl)butyloxyphenyl]-propionic acid or a pharmaceutically acceptable salt, in combination with unfractionated heparin.

Definitions

Unless otherwise indicated, the following terms have the designated meanings:

"Tirofiban" means 2-S-(n-butylsulfonylamino)-3[4-piperidin-4-yl)butyloxyphenyl]propionic acid hydrochloride.

"Pharmaceutically acceptable salts" means non-toxic salts of the compounds (which are generally prepared by reacting the free acid with a suitable organic or inorganic base) which include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

"Therapeutically effective amount" means that amount of a drug or pharmaceutical agent that will elicit the biological or medical response of a tissue, system or animal that is being sought by a researcher or clinician.

"Mammal" includes, within its meaning, primates (e.g. humans, monkeys, etc.), dogs, rabbits, and other species commonly known to be mammals.

The methods of the present invention are useful in combination with procedures for treating patients with other anticoagulants (e.g. thrombin inhibitors such as heparin, Factor Xa inhibitors such as warfarin, tissue factor pathway inhibitors, or thrombin receptor antagonists), thrombolytic agents (e.g. streptokinase and tissue plasminogen activator), and platelet antiaggregation agents (e.g. aspirin and dipyridamole).

The methods are suitable for patients where prevention of thrombosis by inhibition of binding of fibrinogen to the platelet membrane glycoprotein complex IIb/IIIa receptor is desired. Such administration is useful in surgery on peripheral arteries (arterial grafts, carotid endarterectomy) for treatment of peripheral vascular disease, and in cardiovascular surgery where manipulation of arteries and organs, and/or the interaction of platelets with artificial surfaces, leads to platelet aggregation and consumption. Since aggregated platelets may form thrombi and thromboemboli, the methods may be used on these surgical patients to prevent the formation of thrombi and thromboemboli. The GP IIb/IIIa receptor antagonists may also be administered to treat stroke, carotid percutaneous transluminal coronary revascularization, or carotid endarterectomy.

Applications of the methods include prevention of platelet thrombosis, thromboembolism and reocclusion during and after thrombolytic therapy and prevention of platelet thrombosis, thromboembolism and reocclusion after angioplasty or coronary artery bypass procedures, or to improve outcomes following stent implantation (i.e., to prevent thromboembolism on device insertion). It may also be used to treat patients with acute coronary ischemic syndromes including unstable angina and subsequent myocardial infarction.

Low Molecular Weight Heparin

Compositions containing, procedures for making, and methods for using low molecular weight heparin are described in various patent publications, the contents of which are hereby incorporated by reference, including U.S. Pat. Nos. 4,281,108, 4,687,765, 5,106,734, 4,977,250, 5,576,304, and EP 372 969. Commercially available low molecular weight heparin includes FRAGMIN™ (dalteparin sodium injection, available from Pharmacia, Inc. (Columbus, Ohio)) and LOVENOX® (enoxaparin sodium injection, available from Rhone-Poulenc Rorer Pharmaceuticals, Inc. (Collegeville, Pa.), described in EP 040 144).

FRAGMIN™ dalteparin sodium injection is a sterile low molecular weight heparin produced through controlled nitrous acid depolymerization of sodium heparin from porcine intestinal mucosa followed by a chromatographic purification process. It is composed of strongly acidic sulphated polysaccharide chains (oligosaccharide, containing 2,5-anhydro-D-mannitol residues as end groups) with an average molecular weight of 5000 and about 90% of the material within the range 2000–9000. It acts by enhancing the inhibition of Factor Xa and thrombin by antithrombin. It is available in a strength of 2500 anti-Factor Xa IU/0.2 mL. FRAGMIN™ is used for prophylaxis against deep vein thrombosis, which may lead to pulmonary embolism, in patients undergoing abdominal surgery who are at risk for thromboembolic complications, including those over 40 years of age, obese, undergoing surgery under general anesthesia lasting longer than 30 minutes or who have additional risk factors such as malignancy or a history of deep vein thrombosis or pulmonary embolism. Typically, for patients undergoing abdominal surgery, between 1000 and 5000, e.g. 2500 IU should be administered subcutaneously only, each day, and repeated once each day for 5 to 10 days. Dosage adjustment and routine monitoring of coagulation parameters are not required.

LOVENOX® enoxaparin sodium injection is a sterile, low molecular weight heparin produced by alkaline degradation of heparin derived from porcine intestinal mucosa. Its structure is characterized by a 2-O-sulfo-4-enepyranosuronic end group at the non-reducing end of the chain. The substance is the sodium salt. The average molecular weight is 4500. LOVENOX® is used for prevention of deep vein thrombosis, which may lead to pulmonary embolism, following hip or knee replacement surgery. It contains 30 mg enoxaparin sodium in 0.3 mL of Water for Injection, and has an anti-Factor Xa activity of approximately 3000 IU. In patients undergoing hip replacement, or treatment for arterial thrombosis, the recommended dose of LOVENOX Injection is 30 mg twice daily administered by subcutaneous injection with the initial dose given within 12–24 hours post-operatively provided hemostasis has been established. Treatment should be continued throughout the period of post-operative care until the risk of deep vein thrombosis has been diminished.

Glycoprotein IIb/IIIa Antagonists

Antagonists for the glycoprotein IIb/IIIa fibrinogen receptor, along with their therapeutic use, have been described in U.S. Pat. Nos. 5,470,849, 5,463,011, 5,455,243, 5,451,578, 5,446,056, 5,441,952, 5,422,249, 5,416,099, 5,405,854, 5,397,791, 5,393,760, 5,389,631, 5,380,713, 5,374,622, 5,358,956, 5,344,783, 5,340,798, 5,338,7235, 334,596, 5,321,034, 5,318,899 (e.g. cyclic heptapeptides Mpr-(Acetimidyl-Lys)-Gly-Asp-Trp-Phe-Cys-NH$_2$, Mpr-(Acetimidyl-Lys)-Gly-Asp-Trp-Phe-Pen-NH$_2$, Mpr-(Phenylimidyl-Lys)-Gly-Asp-Trp-Phe-Pen-NH$_2$, and Mpr-(Phenylimidyl-Lys)-Gly-Asp-Trp-Phe-Cys-NH$_2$, wherein Mpr is mercapto propionyl), U.S. Pat. No. 5,312,923, 5,294, 616, 5,292,756 (e.g. 2-S-(n-butylsulfonylamino)-3[4-(piperidin-4-yl)butyloxyphenyl]propionic acid and 2-S-(n-butylsulfonylamino)-3[4-(piperidin-4-yl)butyloxyphenyl] propionic acid hydrochloride), U.S. Pat. No. 5,281,585 5,272,158, 5,264,420, 5,260,307, 5,239,113 (e.g. Ethyl 3-[[4-[[4-(aminoiminomethyl)phenyl]amino]-1,4-dioxobutyl]amino]-4-pentynoate), U.S. Pat. Nos. 5,227,490, 5,206,373, 4,703,036 (e.g. N-Methyl-D-phenylalanyl-N-[(1S)-1-formyl-4-guanidinobutyl]-L-prolinamnide), EP 505 868 (e.g. ((1-(2-((4-(aminoiminomethyl)benzoyl)amino)-3-(4-hydroxyphenyl)-1-oxopropyl)-4-piperidinyl)oxy)-(S)-acetic acid), WO 9311152 (e.g. N-(2-(2-(((3-((aminoiminomethyl)amino)propyl)amino)-carbonyl)-1-piperidnyl)-1-(cyclohexylmethyl)-2-oxoethyl)-(R,S)-glycine), EP 333 356 and WO 9422820, WO 95/14683, and WO 94/18981, all of which are herein incorporated by reference, and wherein the scope of this invention includes, but is not limited to, the use of each of the specifically disclosed compounds therein. They are described as useful for inhibiting fibrinogen binding and inhibiting clot formation.

In particular, the GP IIb/IIIa receptor antagonist is selected from: [3(R)-[2-piperidin-4-yl)ethyl]-2-piperidone-1]acetyl-3(R)-methy-b-alanine) described in U.S. Pat. No. 5,281,585; 2(S)-[(p-Toluenesulfonyl)amino]-3-[[[5,6,7,8-tetrahydro-4-oxo-5-[2-(piperidin-4-yl)ethyl]-4H-pyrazolo-[1,5-a][1,4]diazepin-2-yl]carbonyl]-amino]propionic acid described in WO 94/18981; 5-[(4-Piperidinyl)methoxy]-2-indolecarbonyl-2(S)-phenylsulfonyl-amino-b-alanine described in WO 97/15568; and 2-S-(n-butylsulfonylamino)-3[4-piperidin-4-yl)butyloxyphenyl] propionic acid hydrochloride (also known as tirofiban) described in U.S. Pat. No. 5,292,756; DMP 728, described in Circulation, 1996 93:537–543, Cox et al., Medicinal Research Reviews, 1994, 14:195–228, and Cook et al., Drugs of the Future, 1994, 19(2):135–159, from DuPont Merck; DMP 754 ((R)-methyl-3-[[[3-[4-(aminoiminomethyl)phenyl]-4,5-dihydro-5-isoxazolyl] acetyl]amino]-N-(butoxycarbonyl)-L-alanine monoacetate, described in WO 95/14683) from DuPont-Merck; RO44-9883 and RO43-8857, both described in Cook et al., ibid, and Cox et al., ibid, from Hoffman-LaRoche; xemlofiban (also known as xemilofiban) from Searle/Sankyo, described in Circulation, 1995, 92:2331; fradafiban from Boehringer Ingleheim/K. Thomae; SB 2144857 (from SmithKline Beecham); ZD2486 (from Zeneca); TAK 029, described in J. Pharmacology and Experimental Therapeutics, 1996, 277:502–510, from Takeda; orbofiban and SC-58635 from Searle; SC54684, described in Cook et al., ibid, and Cox et al., ibid, from Searle; GR144053, described in Thrombosis and Hematosis, 1993, 69:1071, Cook et al., ibid, and Cox et al., ibid, from Glaxo; compound 109891 from Rhone Polenc Rorer; and sibrafiban from Hoffman-LaRoche as described in EP 656348.

2-S-(n-Butylsulfonylamino)-3[4-(piperidin-4-yl) butyloxyphenyl]propionic acid or pharmaceutically acceptable salts thereof, including tirofiban, described in patent publication U.S. Pat. No. 5,292,756, the contents of which are hereby incorporated by reference, are particularly useful in the present invention. They are described as useful for inhibiting fibrinogen binding, platelet aggregation, and clot formation.

Suitable intravenous compositions of GP IIb/IIIa receptor antagonists, and compositions of low molecular weight heparin, include bolus or extended infusion compositions. Such intravenous compositions are well known to those of ordinary skill in the pharmaceutical arts. In accordance with the invention, for example, 2-S-(n-butylsulfonylamino)-3[4-(piperidin-4-yl)butyloxyphenyl]propionic acid or pharmaceutically acceptable salts thereof and low molecular weight heparin can be administered to the patient together, e.g. in one intravenous solution, or in two separate simultaneously administered solutions. Intravenous administration of the GP IIb/IIIa receptor antagonist and low molecular weight heparin, whether administered together in one solution, or together in two separate solutions, involves preparation of suitable infusion solutions according to procedures well known in the art. Administrations in these various ways are suitable for the present invention as long as the beneficial pharmaceutical effect of the GP IIb/IIIa receptor antagonist and the low molecular weight heparin are realized by the patient at substantially the same time. Such beneficial effect is achieved when the target plasma level concentrations of each active drug ordinarily achieved during independent usage of the drugs are maintained at substantially the same time. Such target plasma level concentrations are readily determined for each patient by persons having ordinary skill in the art.

The dosage regimen utilizing the active drugs is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the therapeutically effective amount of the drug required to prevent, counter, or arrest the progress of the condition.

The active drug can be administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with conventional pharmaceutical practices.

Typically, suitable intravenous solutions of GP IIb/IIIa receptor antagonists, e.g., 2-S-(n-butylsulfonylamino)-3-[4-(4-(piperidin-4-yl)butyloxy)phenyl]propionic acid or pharmaceutically acceptable salts thereof, include pharmaceutically acceptable pH buffers (e.g. sodium citrate), tonicity adjusting agents and other components providing a storage stable and therapeutically effective intravenous solution.

Tonicity adjusting agents, including sodium chloride, are used to adjust tonicity for osmotic pressure and prevent blood cell lysing. These agents minimize pain and thrombophlebitis often experienced by patients receiving intravenous administrations of pharmaceutical compositions. The amount used is that which makes the formulation isotonic with osmotic pressure of the biological system of the patient. Expressed in osmolarity units, the preferred amount of tonicity adjusting agent suitable for the present invention, e.g., sodium chloride, is between about 50–500 milliosmoles, more preferably about 290 milliosmoles. In compositions of the invention, pharmaceutically acceptable osmolarity can be achieved by formulating with an amount of sodium chloride of between about 1.5 and 15 mg/ml, preferably about 9 mg/ml. Such osmolality can also be achieved by using an amount of mannitol of between about 7 and 75 mg/ml, preferably about 50 mg/ml. Other tonicity adjusting agents which can be used to adjust tonicity include, but are not limited to, dextrose and other sugars.

The compositions are not limited to the GP IIb/IIIa receptor antagonist, citrate buffer and tonicity adjusting agent, however, and may also include other pharmaceutically acceptable diluents, excipients or carriers. The formulations are suitable for long-term storage in glass containers commonly used in the pharmaceutical industry, e.g., in concentrated form in standard USP Type I borosilicate glass containers.

In general, the procedure for preparing GPIIb/IIIa receptor antagonist compositions of the invention involves combining the various ingredients in a mixing vessel, e.g., at room temperature. The active ingredient (in salt or free base form), buffer sources (e.g., citric acid and sodium citrate), and tonicity adjusting agent, are combined to obtain an active ingredient concentration of between about 0.01 mg/ml and 0.5 mg/ml.

In one procedure for preparing such compositions, a substantial portion of the finished product amount of water (e.g., between about 60 and 100%) is introduced into a standard pharmaceutical mixing vessel. An amount of active ingredient suitable for obtaining the desired finished product concentration is dissolved in the water. Amounts of sodium citrate and citric acid sufficient to obtain a finished citrate concentration of between about 2 and 20 mM, are added. A pharmaceutically acceptable amount of tonicity adjusting agent in the isotonic range, is added. Any remaining portion of water is then added to achieve the desired final concentrations of ingredients. The amount of water initially used in preparing the formulation, and the amount of the remaining portion of water added at the end of the procedure, does not affect the properties of the finished product. Such amounts are a matter of choice for the skilled artisan, allowing for pH adjustment during formulation.

Concentrated formulations of the compositions can be diluted at the time of administration with a suitable diluent to obtain a finished concentration, for example, of about 0.05 mg/ml, which is suitable for transfer to an infusion bag and use by the patient in need of the desired active ingredient.

Intravenously, the most preferred doses of 2-S-(n-butylsulfonylamino)-3-[4-(4-(piperidin-4-yl)butyloxy)phenyl]propionic acid hydrochloride will range from about 0.001 to about 2 $\mu$g/kg/minute during a constant rate of infusion, e.g., 0.1, 0.15, 0.2, and 0.4 $\mu$g/kg/minute. In order to administer such amounts of tirofiban, an intravenous composition having 0.05 mg/ml of active ingredient can be administered at rates of 0.002, 0.003, 0.004 or 0.008 ml/kg/min, respectively. Compositions of the invention containing higher concentrations of active ingredients should be administered at correspondingly lower rates.

Typically, for treating unstable angina pectoris or non-Q-wave myocardial infarction, 2-S-(n-butylsulfonylamino)-3-[4-(4-(piperidin-4-yl)butyloxy)phenyl]propionic acid hydrochloride (tirofiban) is administered intravenously at an initial infusion rate of 0.4 $\mu$g/kg/minute for 30 minutes or as a bolus of 10 $\mu$g/kg over 3 minutes. Upon completion of the initial infusion or bolus, tirofiban is continued at a maintenance infusion rate of 0.10 $\mu$g/kg/minute. Administration may be continued as needed, e.g. for 48 hours or more (through angiography, and 12 to 24 hours post-angioplasty). In patients in whom tirofiban is initiated in the setting of angioplasty/atherectomy, tirofiban should be administered intravenously as an initial bolus of 10 $\mu$g/kg administered over 3 minutes followed by a maintenance infusion rate of 0.15 $\mu$g/kg/minute.

GP IIb/IIIa receptor antagonists which are orally active are also suitable for purposes of the present method. Dosages of such antagonists, when used for the indicated effects, will range between about 0.005 mg per kg of body weight per day (mg/kg/day) to about 50 mg/kg/day and preferably 0.005–20 mg/kg/day and most preferably 0.005–10 mg/kg/day. Suitable oral tablets contain between 0.5 mg and 5 g, preferably between 0.5 mg and 2 g, most preferably between 0.5 mg and 1 g, e.g. 50 mg, 150 mg, 250 mg, or 500 mg. Oral administration may be in one or divided doses of two, three, or four times daily.

For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Oral compositions of the GP IIb/IIIa receptor antagonists with enteric coatings may be prepared by mixing the antagonist with an excipient to form a spheroid, and coating the spheroid with a thin polymer film. For example, the antagonist is mixed with non-water swellable microcrystalline cellulose to form a spheroid which is then coated with a film of hydroxypropyl methyl cellulose phthalate and or a plasticizer which prevents any release of the antagonist in the stomach. When the composition reaches the intestine, the antagonist is released.

The oral compositions may also be prepared by mixing the antagonist with a wetting agent such as fatty acid esters, lecithin, sucrose, mannitol or sorbitol and then spheronizing or granulating the mixture into microgranules. These are then coated with a microporous membrane polymer such as Eudragit® E30D (Rohm Pharma GmbH, Weiterstadt, Germany), hydroxypropyl methyl cellulose phthalate and other wetting agents, plasticizers and the like. The formulations are enteric by nature and the antagonist does not become bioavailable until the system reaches the intestine.

The compositions may also be prepared by mixing the antagonist and an acid such as fumeric or tartaric acid which is compressed into a spherical tablet and coated with lacquers that are insoluble in gastric juices and soluble in intestinal juices. These lacquers include copolymers of acrylic acid and methacrylic acid esters. The acidic matrix prevents quick dissolution early and yet promotes the antagonist's bioavailability further downstream in the digestive tract.

The compositions may also be prepared by coating a solid dosage form of the antagonist with hydroxypropyl methyl cellulose phthalate or acidic succinyl and acetyl esters of hydroxypropyl methyl cellulose. Triethylcitrate is added as a plasticizer which aids in the binding of the coating material to the core pellet. The coating resists dissolution in the stomach but completely dissolves in the small intestine.

Suitable materials for providing enteric coatings include, for example, hydroxypropyl methyl cellulose phthalate, hydroxypropylmethyl cellulose acetate succinate, hydroxypropyl methyl cellulose phthalate, hydroxypropyl methyl cellulose hexahydrophthalate, shellac, cellulose acetate, cellulose acetate phthalate, polyvinyl acetate phthalate, carboxymethyl ethyl cellulose, methacrylic acid copolymers, methacrylic ester copolymers and the like.

In general, solid dosage forms comprising the antagonist may be coated using conventional coating techniques such as conventional pan coating techniques or column spray coating techniques.

For example, coating pans, e.g. subglobular, pear shaped or hexagonal pans, which are inclined are set to rotate at an appropriate setting sufficient to allow uncoated tablets to be exposed to spray solutions of the polymer used to form the coat. The pan is heated to a sufficient temperature to allow the coat to dry soon after contact with the outside of the tablet.

Some pans have a cylindrical shape, are rotated horizontally, and have at least some regions of the walls perforated by small holes or slots. This design permits a one-way air flow through the pan. In other designs the flow of air is through the tablet bed and out through the perforated wall of the pan. In others the air flows from the perforated pan wall through the tablet bed into the central region, i.e., countercurrent to the coating spray direction. Still others permit either co- or counter-current air flow to suit particular products.

The coating is sprayed in one of several methods. One method relies entirely on hydraulic pressure to produce a spray when material is forced through a nozzle (airless spraying). In another method, atomization of the spray is assisted by turbulent jets of air. This method tends to produce a more easily controlled spray pattern and is therefore better for small-scale operations, although both are capable of giving the flat jet profile preferred for pan operation.

The thickness of coating required on the granules depends on the dissolution profile of the particular coating materials. The coating can contain a plasticizer and possibly other coating additives such as coloring agents, gloss producers, talc and/or magnesium stearate.

The antagonists can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Antagonists may also be delivered by the use of monoclonal antibodies as individual carriers to which the compound molecules are coupled. Antagonists may also be coupled with soluble polymers as targetable drug carriers. Such polymers can include polyvinyl-pyrrolidone, pyran copolymer, polyhydroxy-propyl-methacrylamide-phenol, polyhydroxy-ethyl-aspartamide-phenol, or polyethylene oxide-polylysine substituted with palmitoyl residues. Furthermore, antagonists may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

In ocular formulations such as eyedrops, from about 0.01–5.0% (w/v) of antagonist can be employed, e.g., from about 0.01–2.0% (w/v) of antagonist. Suitable eyedrop volume is, for example, 20, 30, 35, 50 or 100 ml. The objective is to administer a dose of between about 0.005–0.5 mg/kg per day to each eye, for a total dosage of between about 0.01–1.0 mg/kg/day, e.g. a dose of about 0.05 mg/kg per day to each eye, for a total dosage of about 0.1 mg/kg/day. For example, the eyedrops can be used to provide doses of 1 mg, 10 mg, or 50 mg. These dosage values are based on known and presently understood pharmacology of the antagonist. Dosage requirements are variable and must be individualized on the basis of the disease and the response of the patient.

Suitable eyedrop formulations are those which are isotonic and maintain sufficient contact with the eye surface to systemically deliver the active agent to the patient. Such formulations advantageously have a pH approximating neutrality and are non-irritating to the eye, e.g. they do not induce tearing and consequential flow of active agent out of the eye. Pharmaceutically acceptable carriers are, for example, water, mixtures of water and water-miscible solvents such as lower alkanols or arylalkanols, vegetable oils, polyalkylene glycols, petroleum based jelly, ethyl cellulose, hydroxy ethyl cellulose, ethyl oleate, carboxymethylcellulose, polyvinylpyrrolidone, isopropyl myristate and other conventionally-employed non-toxic, pharmaceutically acceptable organic and inorganic carriers. The pharmaceutical preparation may also contain non-toxic auxiliary substances such as emulsifying, preserving, wetting agents, bodying agents and the like, as for example, polyethylene glycols 200, 300, 400 and 600, carbowaxes 1000, 1500, 4000, 6000 and 10000, antibacterial compounds, phenylmercuric salts known to have cold sterilizing properties and which are non-injurious in use, thimerosal, methyl and propyl paraben, benzyl alcohol, phenyl ethanol, buffering ingredients such as sodium chloride, sodium borate, sodium acetates, gluconate buffers, and other conventional ingredients such as sorbitan monolaurate, triethanolamine, oleate, polyoxyethylene sorbitan monopalmitylate, dioctyl sodium sulfosuccinate, monothioglycerol, thiosorbitol, ethylenediamine tetraacetic acid, and the like. Additionally, suitable ophthalmic vehicles can be used as carrier media for the present purpose including conventional phosphate buffer vehicle systems, isotonic boric acid vehicles, isotonic sodium chloride vehicles, isotonic sodium borate vehicles and the like.

In the procedure for making eyedrops, formulations are rendered sterile by appropriate means, such as starting the preparation procedure with sterile components and proceeding under sterile conditions, irradiating or autoclaving the finished formulation, and the like. Suitable anti microbial agents are also useful for maintaining sterility of the eyedrop.

The ocular preparation may also be a solid insert such as one which, after dispensing the antagonist, remains essentially intact, or a bioerodible insert that is soluble in lacrimal fluids, or otherwise disintegrates. For example, one may use a solid water soluble polymer as the carrier for the antagonist. The polymer used to form the insert may be any water soluble non-toxic polymer, for example, cellulose derivatives such as methylcellulose, sodium carboxymethyl cellulose, hydroxyethylcellulose, hydroxypropylcellulose, hydroxypropylmethyl cellulose, acrylates such as polyacrylic acid salts, ethylacrylates, polyacrylamides, natural products such as gelatin, alginates, pectins, tragacanth, karaya, chondrus, agar, acacia, starch derivatives such as starch acetate, hydroxyethyl starch ethers, hydroxypropyl starch, as well as other synthetic derivatives such as polyvinyl alcohol, polyvinyl pyrrolidone, polyvinyl methyl ether, polyethylene oxide, neutralized carbopol, gellan gum and xanthan gum, and mixtures of said polymers.

The ocular preparation may also be an ointment which is compounded, for example, by mixing finely milled powdered ingredients with a small amount of white petrolatum and levigating or otherwise mixing until a uniform distribution is achieved. The balance of white petrolatum is added by geometric addition until the desired dosage form is made.

The present invention is demonstrated in a study of patients with acute coronary ischemic syndromes. Such patients may undergo early coronary revascularization with percutaneous coronary angioplasty or atherectomy. Acute coronary ischemic syndrome is associated with unstable angina, nonfatal myocardial infarction, and death, and subsequent follow-up procedures such as coronary artery bypass grafting, repeat percutaneous intervention for acute ischemia, and insertion of a coronary endovascular stent. Because of unstable plaque with thrombus, percutaneous revascularization procedures in these patients carry with them considerable higher morbidity than procedures performed in patients with stable coronary disease. In accordance with the methods of the invention, patients receive 2-S-(n-butylsulfonylamino)-3-[4-(4-(piperidin-4-yl) butyloxy)phenyl]propionic acid or pharmaceutically acceptable salts thereof with low molecular weight heparin and optionally aspirin.

The following examples show that therapeutic levels of unfractionated heparin combined with tirofiban elicit prolongation in bleeding time that is greater than prolongation in bleeding time resulting from administration of therapeutic levels of low molecular weight heparin combined with tirofiban.

EXAMPLE 1

A patient is treated for unstable angina by intravenously receiving tirofiban in an amount of 0.4 μg/kg/min for 30 minutes followed by 0.1 μg/kg/min for 47.5–107.5 hours. During tirofiban therapy, LOVENOX® enoxaparin is subcutaneously administered in an amount of 1 mg/kg every 12 hours.

EXAMPLE 2

A patient is treated for non-Q wave myocardial infarction by intravenously receiving tirofiban in an amount of 0.4 μg/kg/min for 30 minutes followed by 0.1 μg/kg/min for 47.5–107.5 hours. During tirofiban therapy, LOVENOX® enoxaparin is subcutaneously administered in an amount of 1 mg/kg every 12 hours.

EXAMPLE 3

In a dog, the effects of 1 μg/kg/min tirofiban, a bolus dose of 700 μg/kg of low molecular weight heparin followed by intravenous infusion of 7 μg/kg/min of low molecular weight heparin, and a bolus dose of 5 mg/kg of aspirin, individually and in combination, on template bleeding times, were measured after the initiation of infusions. Bleeding time was measured using a SIMPLATE® bleeding time device (Organon Teknika Corporation, Durham, N.C.) to make incisions on the mucous membrane of the inner, upper lip of the dog and were measured for a maximum of 20 minutes. Activated partial thromboplastin times (APTT, ex vivo measurement of intrinsic coagulation pathway in plasma) and activated clotting times (ACT, ex vivo measurement of intrinsic coagulation pathway in whole blood) were determined as an indication of the function of the clotting factors. Following blood collection and centrifugation, plasma for APTT determination was removed and stored on ice for later assay. APTTs were determined using an automated clot timer (ELECTRA 900, Medical Laboratory Automation, Mt. Vernon, N.Y.) and commercially available reagents (American Dade, Aquada, Puerto Rico), ACTs were measured and determined immediately using fresh, unanticoagulated whole blood (ACT II, Medtronic HemoTec, Inc., Parker, Colo.) AntiXa activity was determined using a colorimetric assay with the Stachrom® Heparin kit (MLA Electra 900C). Whole blood platelet counts were determined using an automated hematology analyzer (Biochem Immunosystems, Allentown, Pa. The concentration of tirofiban in dog plasma was obtained by radioimmunoassay.

90 minutes following initiation of treatment, the three-way combination of tirofiban, low molecular weight heparin and aspirin (TLA) showed greater bleeding times than tirofiban + low molecular weight heparin (TL) or aspirin + low molecular weight heparin (AL). Results obtained by substituting unfractionated heparin (H) for low molecular weight heparin are compared below:

Bleeding times in anaesthetized dogs at 90 minutes

TLA—3.1 minutes
THA—7.3 minutes
TL—1.7 minutes
TH—5.3 minutes
AL—1.5 minutes
AH—8.0 minutes The study results indicate that use of low molecular weight heparin in combination with tirofiban provides reduced prolongation of bleeding time as compared to the use of unfractionated heparin in combination with tirofiban.

EXAMPLE 4

Intravenous formulations

An intravenous dosage form of tirofiban is prepared as follows:

| | |
|---|---|
| Tirofiban | 0.5–100.0 mg |
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

EXAMPLE 5

Intravenous formulations

A pharmaceutical composition was prepared at room temperature using tirofiban, a citrate buffer, and sodium chloride, to obtain a concentration of tirofiban of 0.25 mg/ml.

800 grams of water was introduced into a standard pharmaceutical mixing vessel. 0.25 grams of tirofiban was dissolved in the water. 2.7 grams sodium citrate and 0.16 grams citric acid were added to obtain a finished citrate concentration of 10 mM. 8 grams of sodium chloride was added. 200 grams of water was then added to achieve the desired final concentrations of ingredients. The resulting aqueous formulation had the following concentrations:

| Ingredient | Amount |
|---|---|
| Tirofiban | 0.25 mg/ml |
| citrate buffer | 10 mM |
| sodium chloride | 8 mg/ml |

The finished concentrated formulation is stored in a standard USP Type I borosilicate glass container at 30–40 degrees C. Prior to compound administration, the concentrated formulation is diluted in a 4:1 ratio resulting in a finished concentration of 0.05 mg/ml and transferred to an infusion bag.

What is claimed is:

1. A method for inhibiting platelet aggregation in a mammal comprising administering to the mammal a safe and therapeutically effective amount of a GPIIb/IIIa receptor antagonist or a pharmaceutically acceptable salt thereof and a safe and therapeutically effective amount of low molecular weight heparin.

2. A method of claim 1 for inhibiting platelet aggregation in a mammal wherein the GP IIb/IIIa receptor antagonist is (2-S-(n-butylsulfonylamino)-3[4-(piperidin-4-yl) butyloxyphenyl]propionic acid or a pharmaceutically acceptable salt thereof.

3. A method for inhibiting platelet aggregation in a mammal comprising administering to the mammal a safe and therapeutically effective amount of a GPIIb/IIIa receptor antagonist or a pharmaceutically acceptable salt thereof, a safe and therapeutically effective amount of low molecular weight heparin, and a safe and therapeutically effective amount of aspirin.

4. A method of claim 3 for inhibiting platelet aggregation in a mammal wherein the GP IIb/IIIa receptor antagonist is (2-S-(n-butylsulfonylamino)-3[4-(piperidin-4-yl) butyloxyphenyl]propionic acid or a pharmaceutically acceptable salt thereof.

5. A method for inhibiting platelet aggregation in a patient comprising administering to the patient a therapeutically effective amount of a GP IIb/IIIa receptor antagonist or a pharmaceutically acceptable salt thereof and a therapeutically effective amount of a low molecular weight heparin, wherein bleeding time is reduced relative to bleeding time associated with a method comprising administration of unfractionated heparin.

* * * * *